United States Patent
Hsu et al.

(10) Patent No.: US 8,034,111 B2
(45) Date of Patent: Oct. 11, 2011

(54) ADJUSTABLE VERTEBRAL SPACER FOR VERTEBRAL RECONSTRUCTION

(75) Inventors: Wen-Hsien Hsu, Taishan Township, Taipei County (TW); Hsi-Ching Hsu, Jhongli (TW); Ching-Chi Hsu, Jhudong Township, Hsinchu County (TW); Yu-Hsiang Tsai, Taipei (TW); Kao-Shang Shih, Taipei (TW); Long-Ming Lu, Yilan (TW)

(73) Assignees: Ching-Kong CHAO (TW); Wen-Hsien HSU (TW); Hsi-Ching HSU (TW); Yu-Hsiang TSAI (TW)

( * ) Notice: Subject to any disclaimer, the term of this patent is extended or adjusted under 35 U.S.C. 154(b) by 603 days.

(21) Appl. No.: 12/076,363

(22) Filed: Mar. 17, 2008

(65) Prior Publication Data

US 2009/0164019 A1    Jun. 25, 2009

(30) Foreign Application Priority Data

Nov. 30, 2007 (TW) ................................ 96145537 A (51) Int. Cl.
*A61F 2/44* (2006.01)
(52) U.S. Cl. ................. 623/17.15; 623/17.11; 623/17.16

(58) Field of Classification Search .......... 606/246–279; 623/17.11–17.16
See application file for complete search history.

(56) References Cited

U.S. PATENT DOCUMENTS

| | | | |
|---|---|---|---|
| 2005/0085910 A1* | 4/2005 | Sweeney | 623/17.11 |
| 2005/0113831 A1* | 5/2005 | Franck et al. | 606/61 |
| 2005/0187634 A1* | 8/2005 | Berry | 623/17.15 |
| 2006/0015183 A1* | 1/2006 | Gilbert et al. | 623/17.11 |
| 2006/0074490 A1* | 4/2006 | Sweeney | 623/17.15 |
| 2006/0241770 A1* | 10/2006 | Rhoda et al. | 623/17.15 |
| 2007/0191954 A1* | 8/2007 | Hansell et al. | 623/17.15 |
| 2009/0138089 A1* | 5/2009 | Doubler et al. | 623/17.16 |
| 2010/0094424 A1* | 4/2010 | Woodburn et al. | 623/17.16 |

* cited by examiner

*Primary Examiner* — Eduardo C Robert
*Assistant Examiner* — Nicholas Plionis
(74) *Attorney, Agent, or Firm* — Guice Patents PLLC (57) ABSTRACT

An adjustable vertebral spacer includes a spacer body, a movable member coupled to the spacer body, an adjustment ring mounted on the spacer body and rotatable to move the movable member and to further adjust the combined height of the spacer body and the movable member, a lock ring mounted on the spacer body for locking the movable member to the adjustment ring, and a top endplate coupled to the movable member at the top and tiltable to fit the angle of the adjacent upper vertebral body during surgery operation.

9 Claims, 11 Drawing Sheets

ADJUSTABLE VERTEBRAL SPACER FOR VERTEBRAL RECONSTRUCTION

BACKGROUND OF THE INVENTION

1. Field of the Invention

The present invention relates to a vertebral spacer for artificial vertebrae and more particularly, to an adjustable vertebral spacer that allows adjustment of the height (length) and tilting angle.

2. Description of the Related Art

In a vertebral body replacement, a vertebral spacer for artificial vertebrae is usually used to replace or treat the anterior column of the spine after the resection of spinal tumors or severely fractured anterior spinal elements. By means of a surgery operation the diseased vertebral body is resected, and a vertebral spacer is installed to replace the resected vertebral body, and affixed in place by means of a pedical screw or vertebral plate, resuming the function of the patient's spinal column.

Figure 1A:
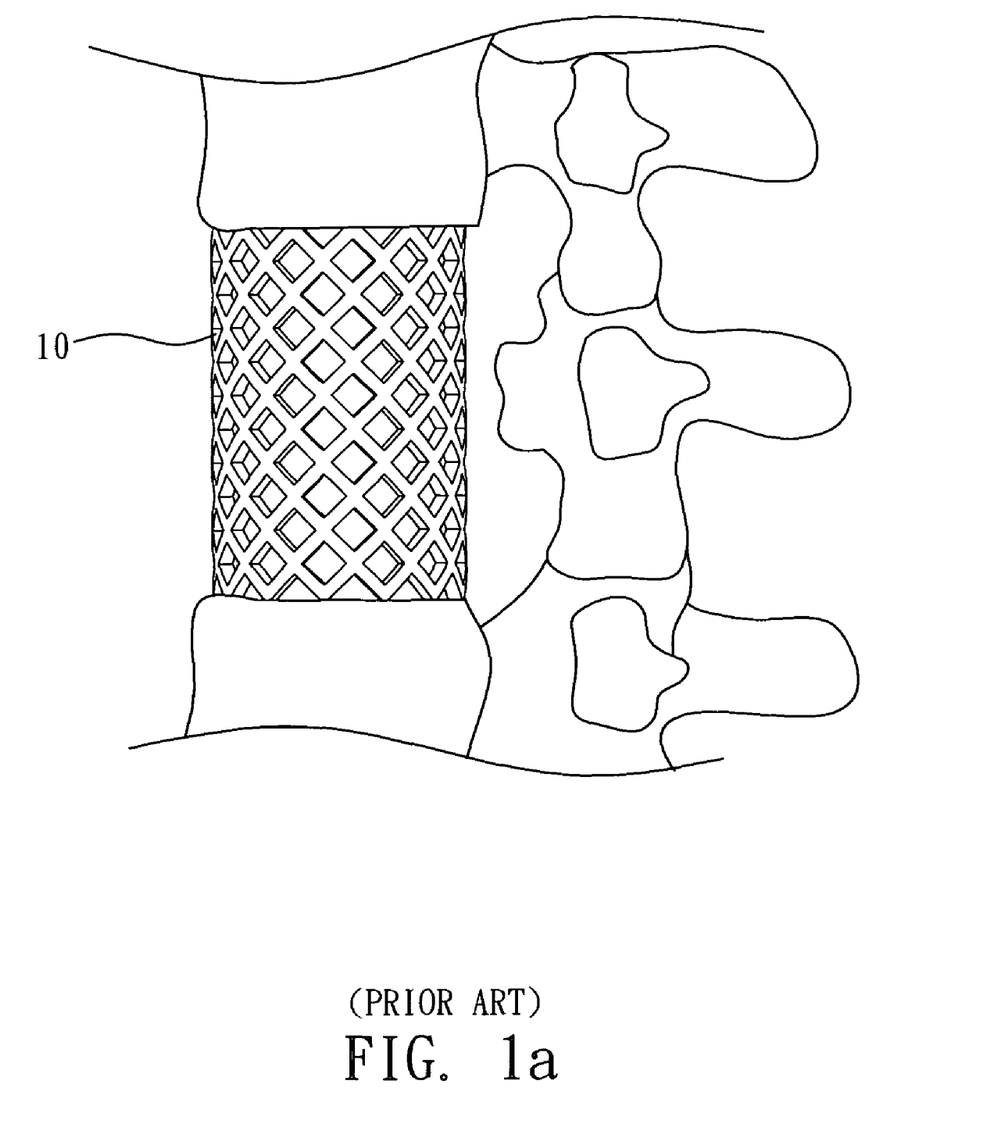
FIG. 1a illustrates a vertebral spacer for artificial vertebrae according to the prior art.

Conventional vertebral spacer designs include two types, i.e., the mesh cage type and the adjustable type. FIG. 1a shows a cage type vertebral spacer 10. The mesh cage type vertebral spacer 10 is properly cut subject to the length of the resected vertebral body so that the vertebral spacer 10 can be set in between the adjacent upper and lower vertebral bodies. The major drawback of this design of mesh cage type vertebral spacer 10 is the non-adjustability of the height, and it needs to be trimmed several times during the surgery operation, wasting much the operation time. Further, the lordosis angle between the horizontal angle-like irregular spikes and the vertebral endplate does not match, and the spikes pierce the vertebral endplate, accelerating sagging.

Figure 1B:
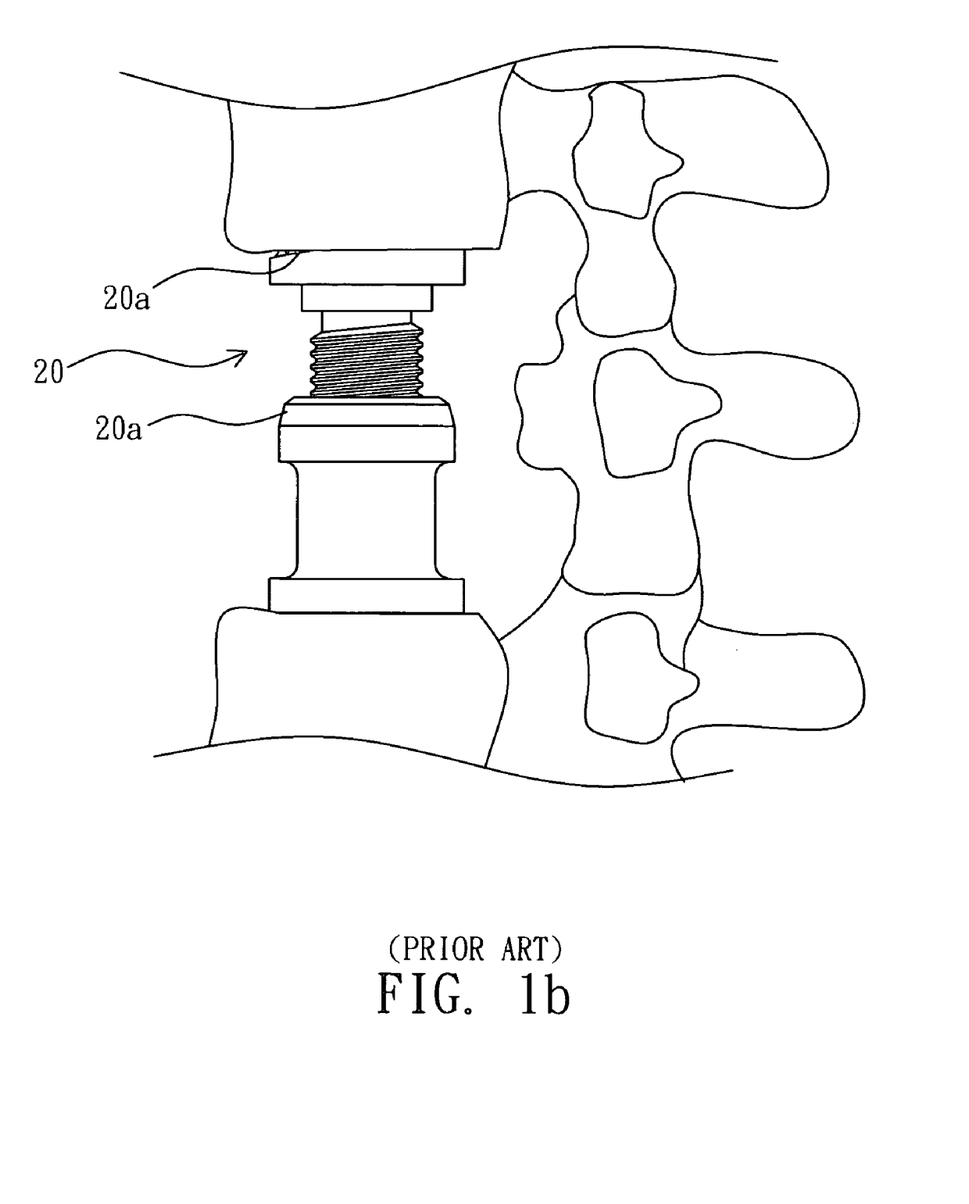
FIG. 1b illustrates another design of vertebral spacer for artificial vertebrae according to the prior art.

FIG. 1b shows an adjustable design of vertebral spacer 20. According to this design, the top and bottom endplates 20a are respectively fastened to the spacer body of the vertebral spacer 20 by means of a screw joint so that the endplates 20a are rotatable to adjust the height of the vertebral spacer 20. However, the fusion and fixation stability between the endplates 20a and the spinal column of the patient determines the successbility of the vertebral body displacement. The reasons of failures in surgical operations using this adjustable design of vertebral spacer 20 include (1) slipping of the adjustable vertebral spacer from the predetermined position, and (2) sagging of the artificial vertebral spacer or piercing the artificial vertebral spacer through the adjacent upper and lower vertebral bodies to cause vertebral destruction.

Therefore, it is desirable to provide a vertebral spacer that eliminates the aforesaid problems.

SUMMARY OF THE INVENTION

The present invention has been accomplished under the circumstances in view. It is the main object of the present invention to provide an adjustable vertebral spacer that allows adjustment of the height and the tilting angle, provides high positioning stability, and practical for use to replace a destructed cervical, thoracic or lumber vertebral body.

To achieve this and other objects and according to one embodiment of the present invention, the adjustable vertebral spacer comprises a spacer body, the spacer body comprising a tubular body wall, a plurality of outer threads extending around the tubular body wall, a tubular space defined within the tubular body wall, a plurality of longitudinal guide slots cut through and downwardly extending from the topmost edge of the tubular body wall, a bottom endplate transversely located at a bottom side of the tubular body wall, a plurality of bottom protrusions downwardly protruding from the bottom endplate, and at least one bone-fusion hole cut through the bottom endplate in communication with the tubular space of the spacer body; an adjustment ring threaded onto the outer threads of the spacer body and rotatable to move vertically upwards and downwards along the spacer body; a movable member vertically movably inserted into the tubular space of the spacer body, the movable member comprising a tubular socket wall, a tubular space defined within the tubular socket wall, a plurality of guide rods perpendicularly extended from the periphery of the tubular socket wall and respectively inserted through the longitudinal guide slots of the spacer body and supported on the adjustment ring for allowing the movable member to be moved with the adjustment ring vertically along the spacer body to a selected elevation through a rotation motion of the adjustment ring relative to the spacer body, a top endplate fixedly provided at a top side thereof, a plurality of top protrusions upwardly protruding from the top endplate, and at least one bone-fusion hole cut through the top endplate in communication with the tubular space of the movable member; and a lock ring threaded onto the outer threads of the spacer body to lock the guide rods of the movable member to the adjustment ring.

According to an alternate form of the present invention, the adjustable vertebral spacer comprises a spacer body, the spacer body comprising a tubular body wall, a plurality of outer threads extending around the tubular body wall, a tubular space defined within the tubular body wall, a plurality of longitudinal guide slots cut through and downwardly extending from the topmost edge of the tubular body wall, a bottom endplate transversely located at a bottom side of the tubular body wall, a plurality of bottom protrusions downwardly protruding from the bottom endplate, and at least one bone-fusion hole cut through the bottom endplate in communication with the tubular space of the spacer body; an adjustment ring threaded onto the outer threads of the spacer body and rotatable to move vertically upwards and downwards along the spacer body; a movable member vertically movably inserted into the tubular space of the spacer body, the movable member comprising a tubular socket wall, a tubular space defined within the tubular socket wall, and a plurality of guide rods perpendicularly extended from the periphery of the tubular socket wall and respectively inserted through the longitudinal guide slots of the spacer body and supported on the adjustment ring for allowing the movable member to be moved with the adjustment ring vertically along the spacer body to a selected elevation through a rotation motion of the adjustment ring relative to the spacer body; a lock ring threaded onto the outer threads of the spacer body to lock the guide rods of the movable member to the adjustment ring; and a top endplate connected to the movable member above the tubular space of the movable member and tiltable relative to the movable member, the top endplate comprising a plurality of top protrusions upwardly protruding from the top endplate, and at least one bone-fusion hole cut through the top endplate in communication with the tubular space of the movable member.

DETAILED DESCRIPTION OF THE PREFERRED EMBODIMENT

Figure 2:
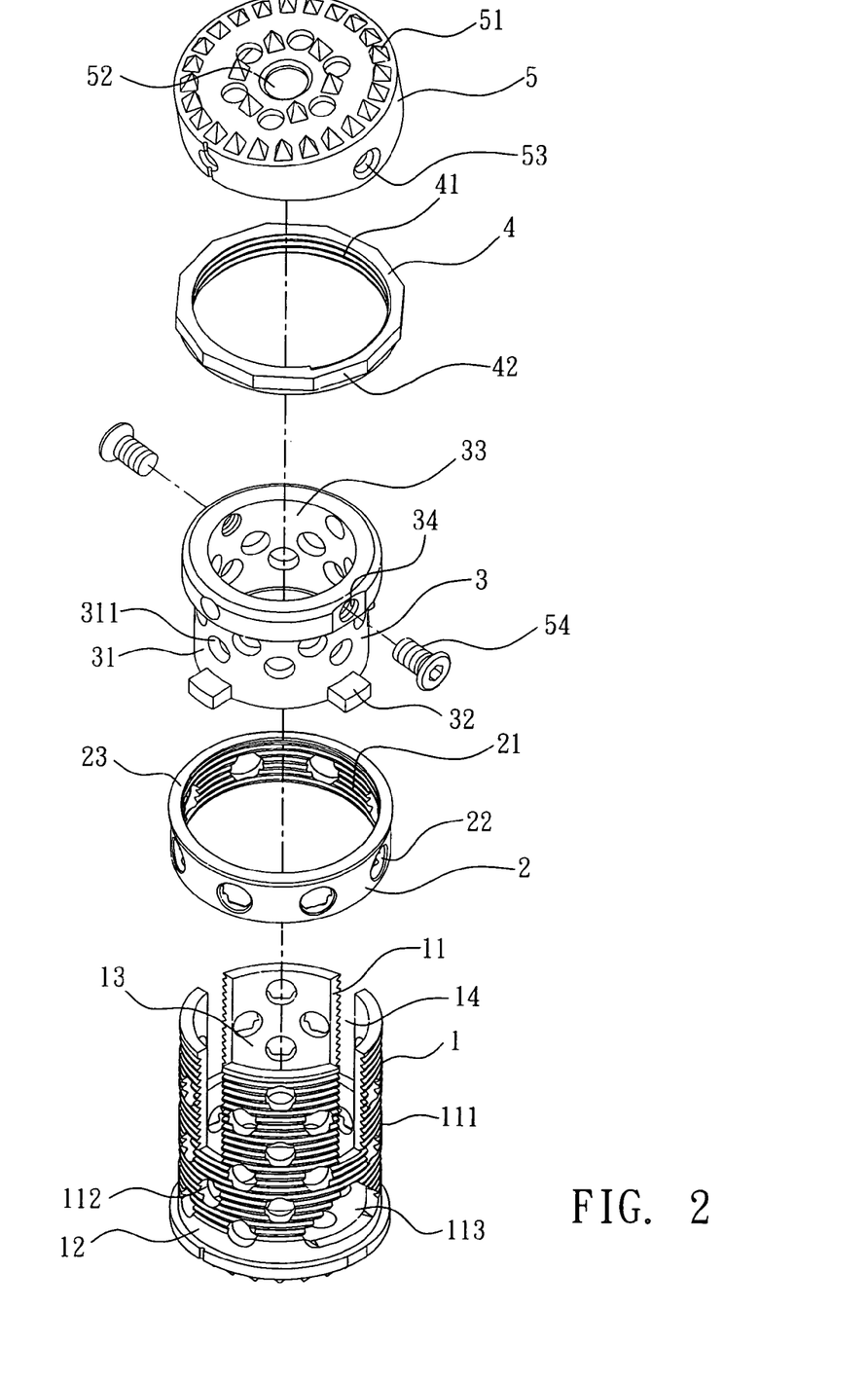
FIG. 2 is an exploded view of an adjustable vertebral spacer for artificial vertebrae in accordance with a first embodiment of the present invention.
Figure 3:
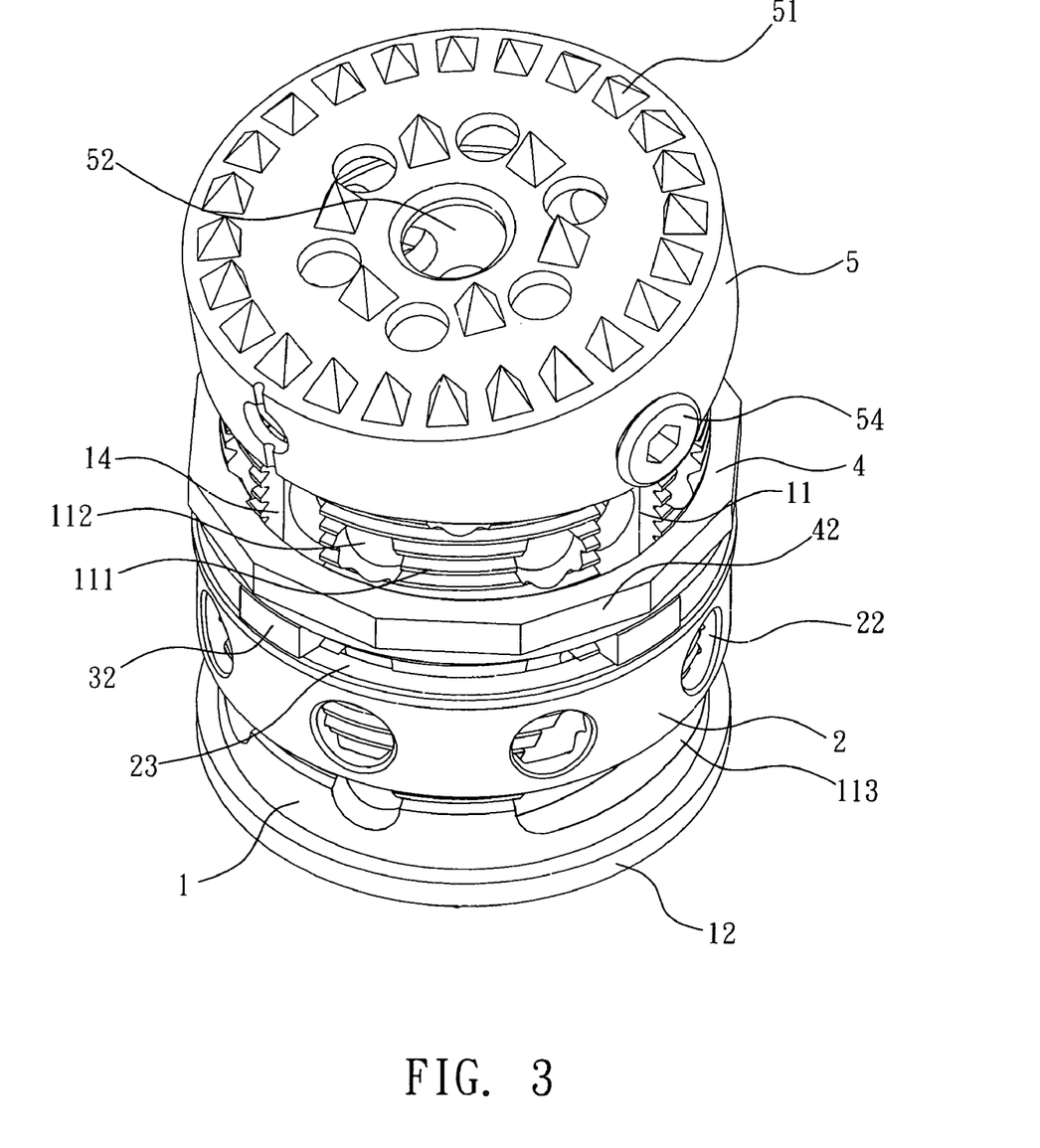
FIG. 3 is an elevational assembly view in an enlarged scale of the adjustable vertebral spacer for artificial vertebrae shown in FIG. 2.
Figure 4:
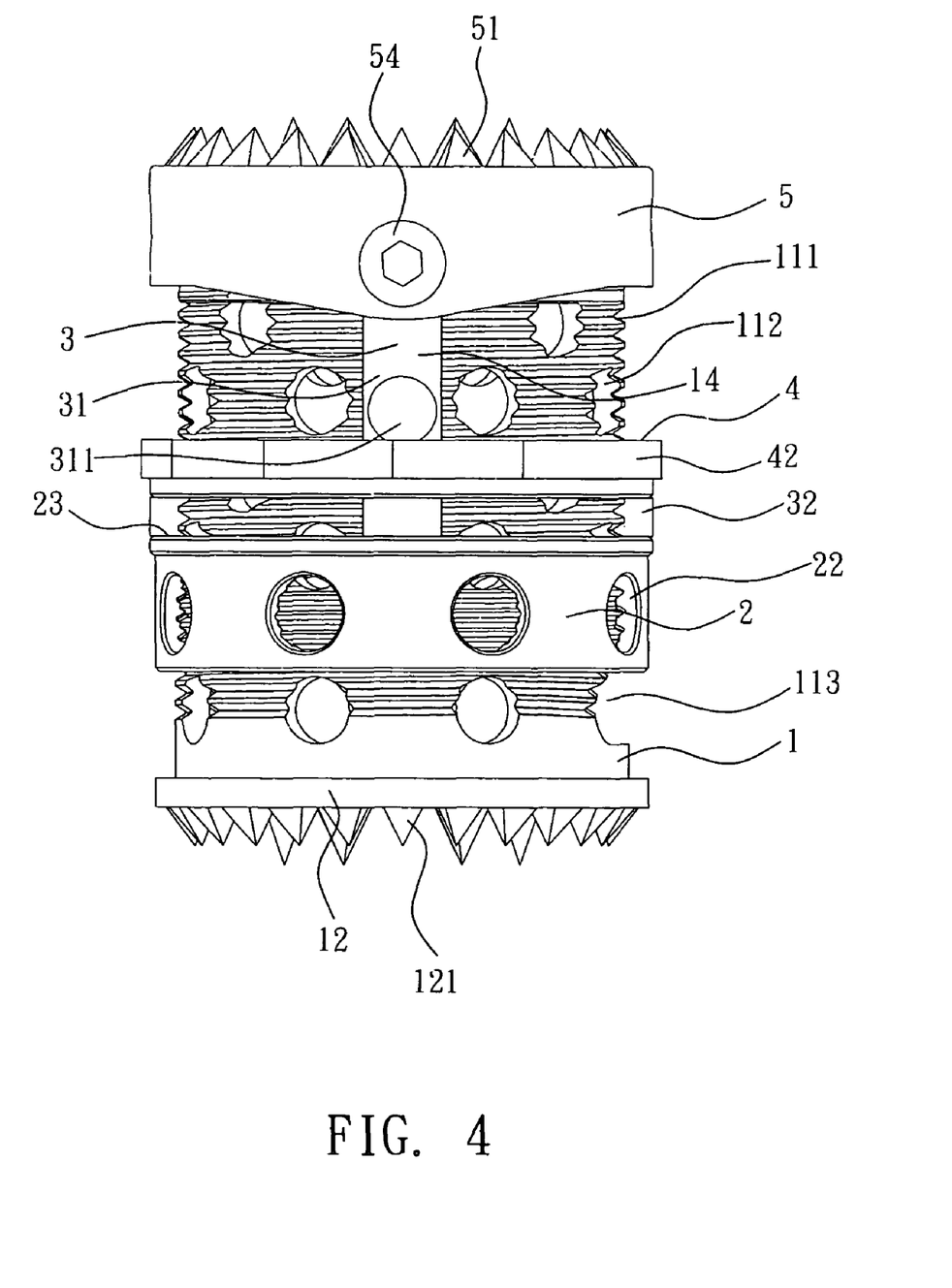
FIG. 4 is a side view of FIG. 3.

Referring to FIGS. 2~4, basically, the adjustable vertebral spacer of the present invention is adapted for use in a cervical, thoracic or lumber vertebrae that has lost its function of supporting the human body. The adjustable vertebral spacer is to be mounted in the space surrounded by the diseased vertebral body and the two adjacent vertebral discs after resection of the diseased vertebral body. By means of the adjustable vertebral spacer to replace the resected vertebral body, the desired human body support function is obtained. The adjustable vertebral spacer is comprised of a spacer body 1, an adjustment ring 2, a movable member 3, and a lock ring 4.

The spacer body 1 is a tubular member made out of, but not limited to, titanium alloy. Following development of biomedical material science, a non-metal material, such as PEEK (poly ether ketone) may be used for making the spacer body 1. The spacer body 1 has a tubular body wall 11, outer threads 111 extending around the tubular body wall 11, a plurality of through holes 112 cut through the tubular body wall 11 and evenly distributed over the whole area of the tubular body wall 11, a bottom endplate 12 transversely located at the bottom side of the tubular body wall 11, a plurality of bottom protrusions 121, for example, pointed teeth downwardly protruding from the bottom side of the bottom endplate 12 (see FIG. 4) for engaging into the vertebral body of the adjacent lower vertebrae to enhance the stability. The number of the through holes 112 is determined subject to the length and dimension of the spacer body 1. The bottom protrusion (pointed teeth) 121 can be shaped like a pyramid or cone. In addition to the bottom protrusion (pointed teeth) 121 at the bottom side of the bottom endplate 12, the bottom endplate 12 is provided with at least one bone-fusion hole (not shown, and will be described further). The bottom endplate 12 may be provided with one single bone-fusion hole of a relatively greater size. Alternatively, the bottom endplate 12 can be provided with multiple bone-fusion holes of a relatively smaller size. The tubular space 13 defined within the tubular body wall 11 is adapted to accommodate crushed self or transplanted bone graft, for enabling the bone graft to grow in the tubular space 13. The tubular space 13 can also be filled with a biomedical material such as bone cement or artificial bone to enhance the support power of the spacer body 1. By means of the at least one bone-fusion hole, the bone graft or biomedical material is kept in contact with the vertebral body of the adjacent lower vertebrae to facilitate bone fusion.

Further, the tubular body wall 11 of the spacer body 1 has at least two longitudinal guide slots 14 downwardly extending from the topmost edge, as shown in FIG. 2. According to this embodiment, the tubular body wall 11 has four equiangularly spaced longitudinal guide slots 14 for guiding vertical movement of the movable member 3 within the tubular space 13 to adjust the combined height of the spacer body 1 and the movable member 3. The spacer body 1 further has a filling hole 113 cut through the tubular body wall 11. The size of the filling hole 113 is relatively greater than the through holes 112. The filling hole 113 can be a triangular hole, rectangular hole or round hole. According to this embodiment, as shown in FIG. 2, the filling hole 113 is a triangular hole. After the adjustable vertebral spacer has been set between the vertebral bodies of the two adjacent vertebraes and adjusted to the desired height, the surgeon can fill the prepared bone graft or biomedical material into the tubular space 13 of the spacer body 1 and the tubular space 33 defined within the movable member 3 through the filling hole 113.

The adjustment ring 2 is an annular member having an inner diameter corresponding to the outer diameter of the tubular body wall 11 of the spacer body 1, inner threads 21 extending around the inside wall for threading onto the outer threads 111 of the spacer body 1, a plurality of through holes 22 cut through and equiangularly spaced around the periphery, and a bearing wall 23 at the top side for supporting the movable member 3. During vertebral body replacement, the perfusion cannula of the perfusion equipment can be inserted through the through holes 22 and 112 to perfuse the prepared bone graft or biomedical material into the tubular space 13.

Figure 5:
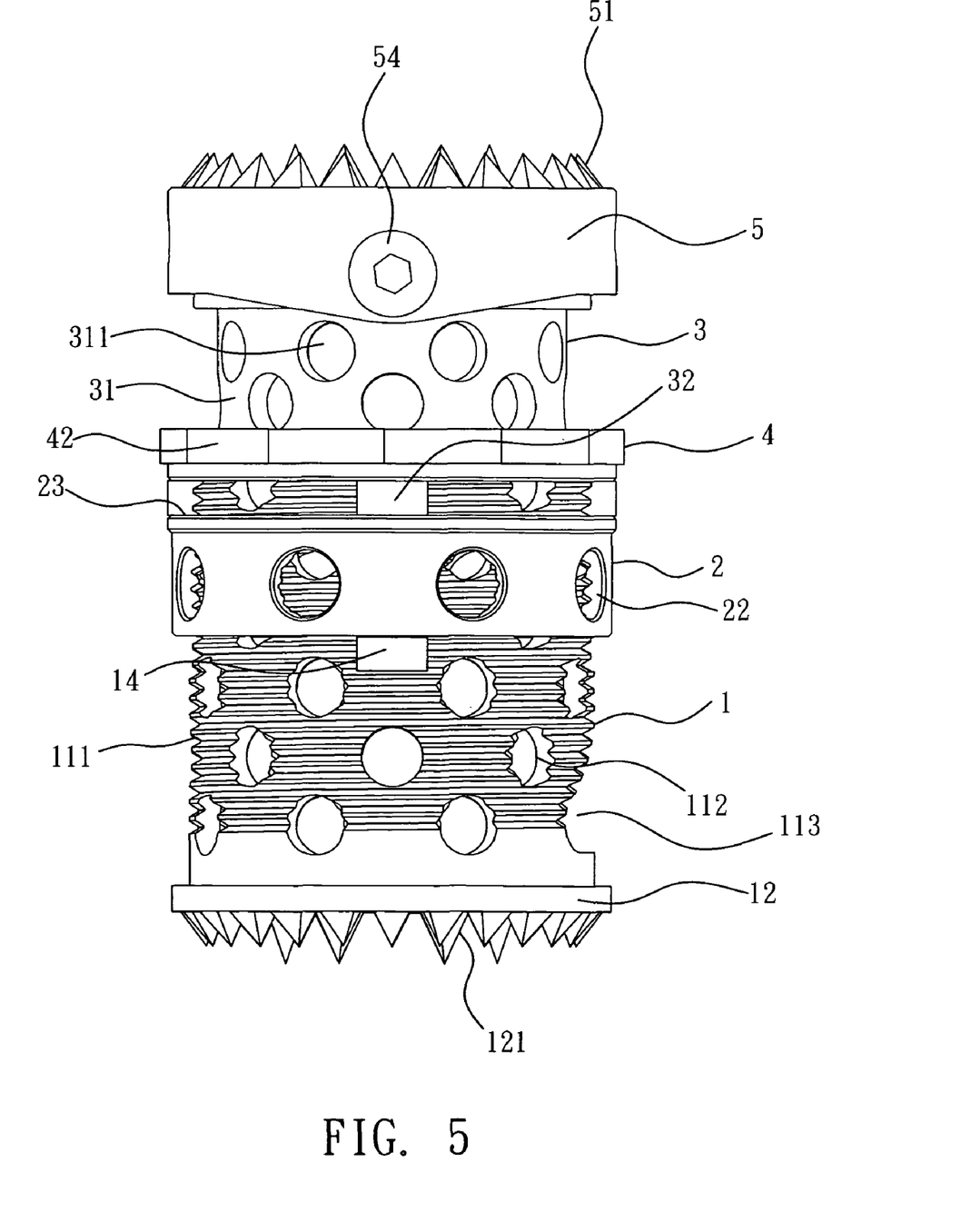
FIG. 5 corresponds to FIG. 4, showing the height of the adjustable vertebral spacer adjusted.

The movable member 3 is a socket having a socket wall 31 of which the outer diameter corresponds to the inner diameter of the spacer body 1 so that the movable member 3 is insertable into the tubular space 13, a plurality of through holes 311 cut through and distributed over the socket wall 31 for the perfusion of the prepared bone graft or biomedical material into the tubular space 33 defined within the socket wall 31, and a plurality of guide rods 32 perpendicularly extended from the socket wall 31 of the spacer body 1 and respectively inserted through the longitudinal guide slots 14 and supported on the top bearing wall 23 of the adjustment ring 2. When wishing to adjust the combined height of the spacer body 1 and the movable member 3, rotate the adjustment ring 2 clockwise or counter-clockwise to lower or lift the top bearing wall 23 vertically relative to the spacer body 1, for enabling the guide rods 32 of the movable member 3 to be moved with the adjustment ring 2 along the longitudinal guide slots 14 between the lower limit position shown in FIG. 4 and the upper limit position shown in FIG. 5.

The lock ring 4 is a lock nut having inner threads 41 extending around the inside wall for threading onto the outer threads 111 of the spacer body 1 and moving longitudinally along the height of the spacer body 1 by means of rotation, and a plurality of mill surface 42 abutted against one another around the periphery for the gripping of a tool to rotate the lock ring 4. After adjustment of the adjustment ring 2 to support the movable member 3 at the desired elevation, the lock ring 4 is rotated downwards toward the guide rods 32, for enabling the guide rods 32 to be sandwiched between the top bearing wall 23 of the adjustment ring 2 and the bottom edge of the lock ring 4, holding the movable member 3 firmly at the desired elevation.

The adjustable vertebral spacer further comprises a top endplate 5 for direct contact with the vertebral body of the adjacent upper vertebrae to enhance the stability. As shown in FIG. 2, the top endplate 5 has a plurality of top protrusions 51, for example, pointed teeth upwardly protruding from the top side for engaging into the vertebral body of the adjacent upper vertebrae to enhance the stability. The top protrusion (pointed teeth) 51 can be shaped like a pyramid or cone. In addition to the top protrusion (pointed teeth) 51, the top endplate 5 is provided with at least one bone-fusion hole 52. The top endplate 5 may be provided with one single bone-fusion hole of a relatively greater size. Alternatively, the top endplate 5 can be provided with multiple bone-fusion holes of a relatively smaller size. During filling of the prepared bone graft or biomedical material into the tubular space 33 of the movable member 3, the bone graft or biomedical material is forced through the at least one bone-fusion hole 52 into direct contact with the vertebral body of the adjacent upper vertebrae to facilitate bone fusion.

Figure 6:
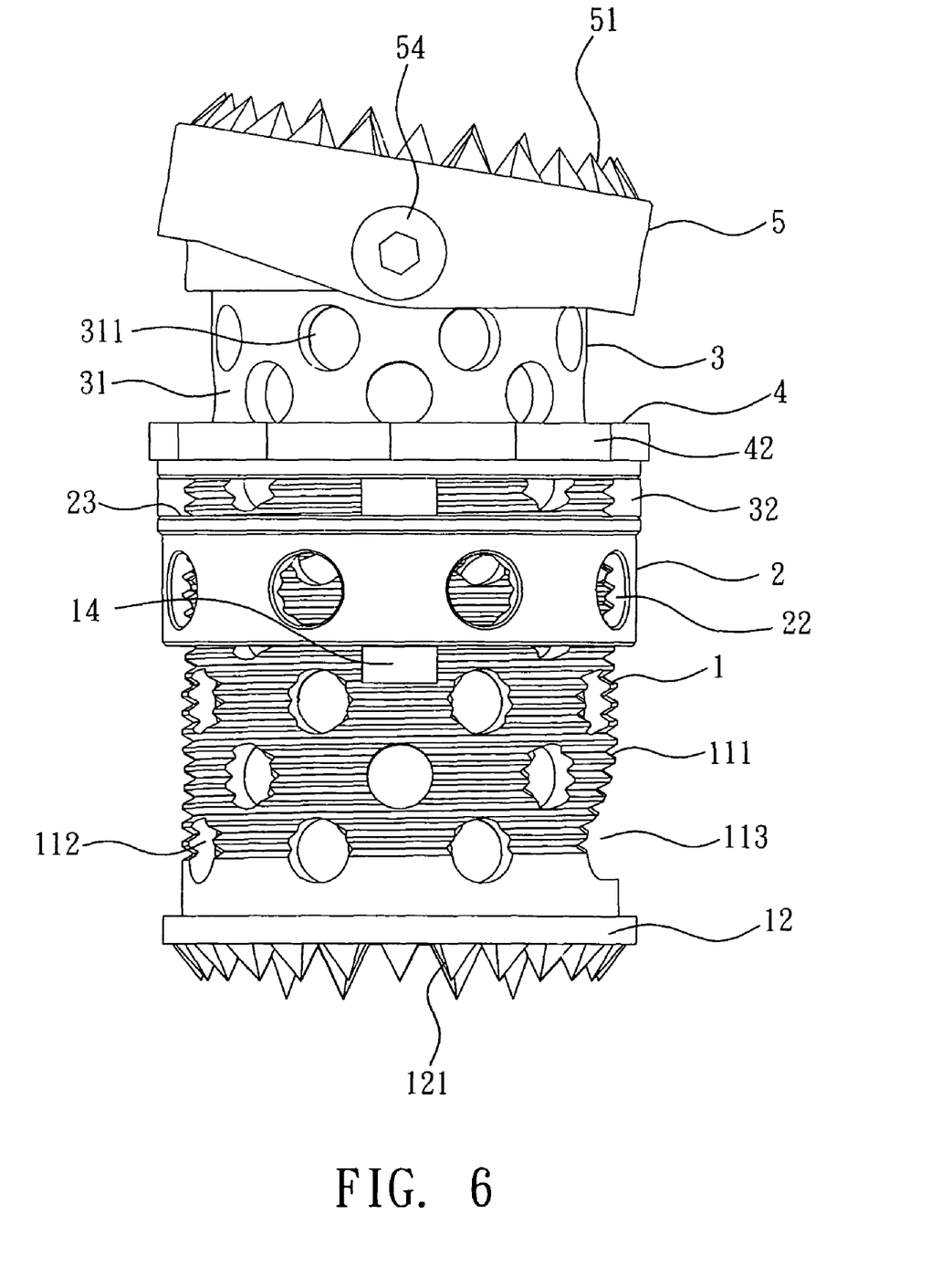
FIG. 6 corresponds to FIG. 5, showing the tilting angle of the top endplate adjusted.

To fit the tilting angle of the vertebraes of the patient, the tilting angle of the top endplate 5 is adjustable. According to this embodiment, the top endplate 5 is a cap member pivotally and tiltably capped on the top side of the movable member 3. After the movable member 3 has been adjusted to the desired elevation, the top endplate 5 is tilted to the best optimal tilting angle to fit the tilting angle of the tilting angle of the vertebral body of the adjacent upper vertebrae. As shown in FIG. 2, the top endplate 5 has two pivot holes 53 horizontally aligned at two opposite sides corresponding two opposite mounting through holes, for example, screw holes 34 on the movable member 3. Two pivot members, for example, pivot bolts 54 are respectively inserted through the pivot holes 53 and fastened to the mounting through holes 34 to lock the top endplate 5 to the movable member 3. Before fastening up the pivot bolts 54, the top endplate 5 can be tilted relative to the movable member 3, as shown in FIG. 6.

Figure 7:
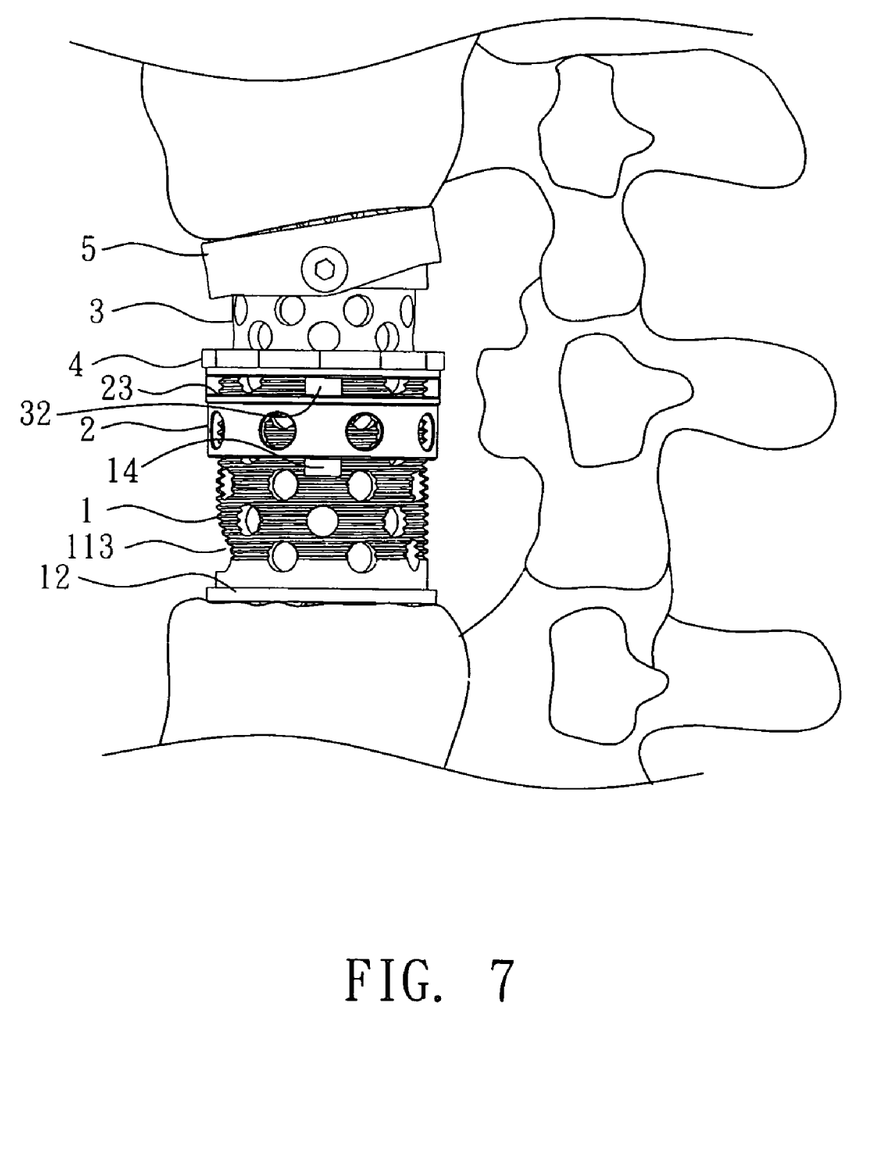
FIG. 7 is a schematic applied view of the first embodiment of the present invention, showing the adjustable vertebral spacer connected between two vertebral bodies.

In the example shown in FIG. 7, the vertebral body of the diseased third lumber vertebrae and the vertebral disc between the second and third lumbar vertebraes as well as the vertebral disc between the third and fourth vertebraes have been has been resected, and the adjustable vertebral spacer is set into place to displace the resected vertebral body. Thereafter, rotate the adjustment ring 2 to move the top bearing wall 23 vertically along the height of the spacer body 1, causing the guide rods 32 to be moved with the top bearing wall 23 of the adjusting ring 2 along the longitudinal guide slots 14, and therefore the movable member 3 is moved vertically to the desired elevation. After adjustment of the movable member 3 to the desired elevation, the lock ring 4 is rotated in the reversed direction toward the guide rods 32 to have the guide rods 32 to be sandwiched between the top bearing wall 23 and the lock ring 4, thereby locking the movable member 3 to the adjusted elevational position where the top endplate 5 and the bottom endplate 12 are respectively abutted against the respective adjacent vertebral bodies. At this time, the top endplate 5 is automatically tilted to fit the bottom side of the corresponding vertebral body, and the bottom protrusions 121 and the top protrusions 51 are respectively and partially engaged into the respective vertebral bodies. After displacement, the adjustable vertebral spacer displaces the resected vertebral body, providing human body support function to support the body of the patient. Therefore, the adjustable vertebral spacer does not slip from the patient's spine, effectively prevents vertebral sagging and accelerating bone fusion.

Figure 8:
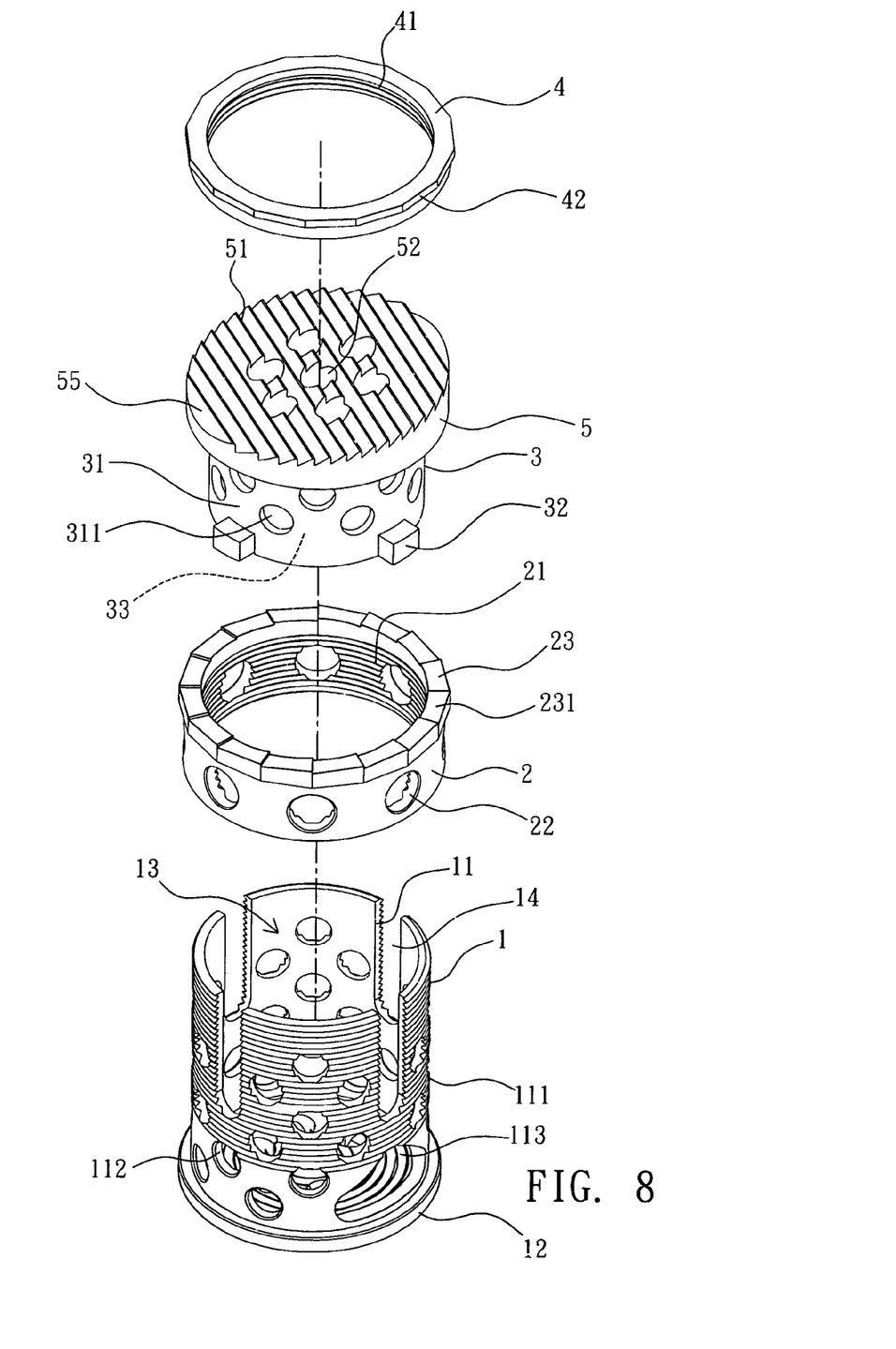
FIG. 8 is an exploded view of an adjustable vertebral spacer for artificial vertebrae in accordance with a second embodiment of the present invention.
Figure 9:
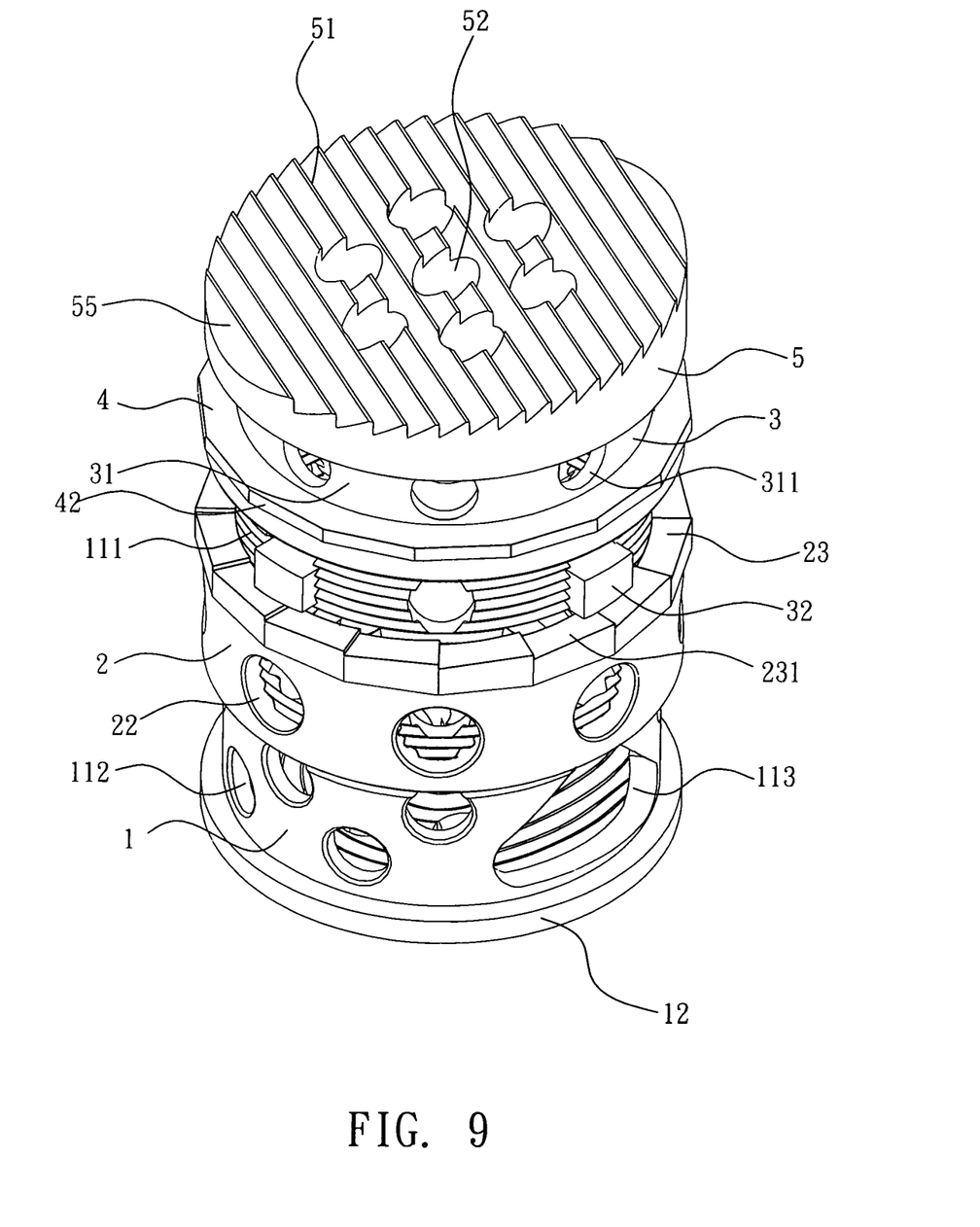
FIG. 9 is an elevational assembly view in an enlarged scale of the adjustable vertebral spacer for artificial vertebrae shown in FIG. 8.
Figure 10:
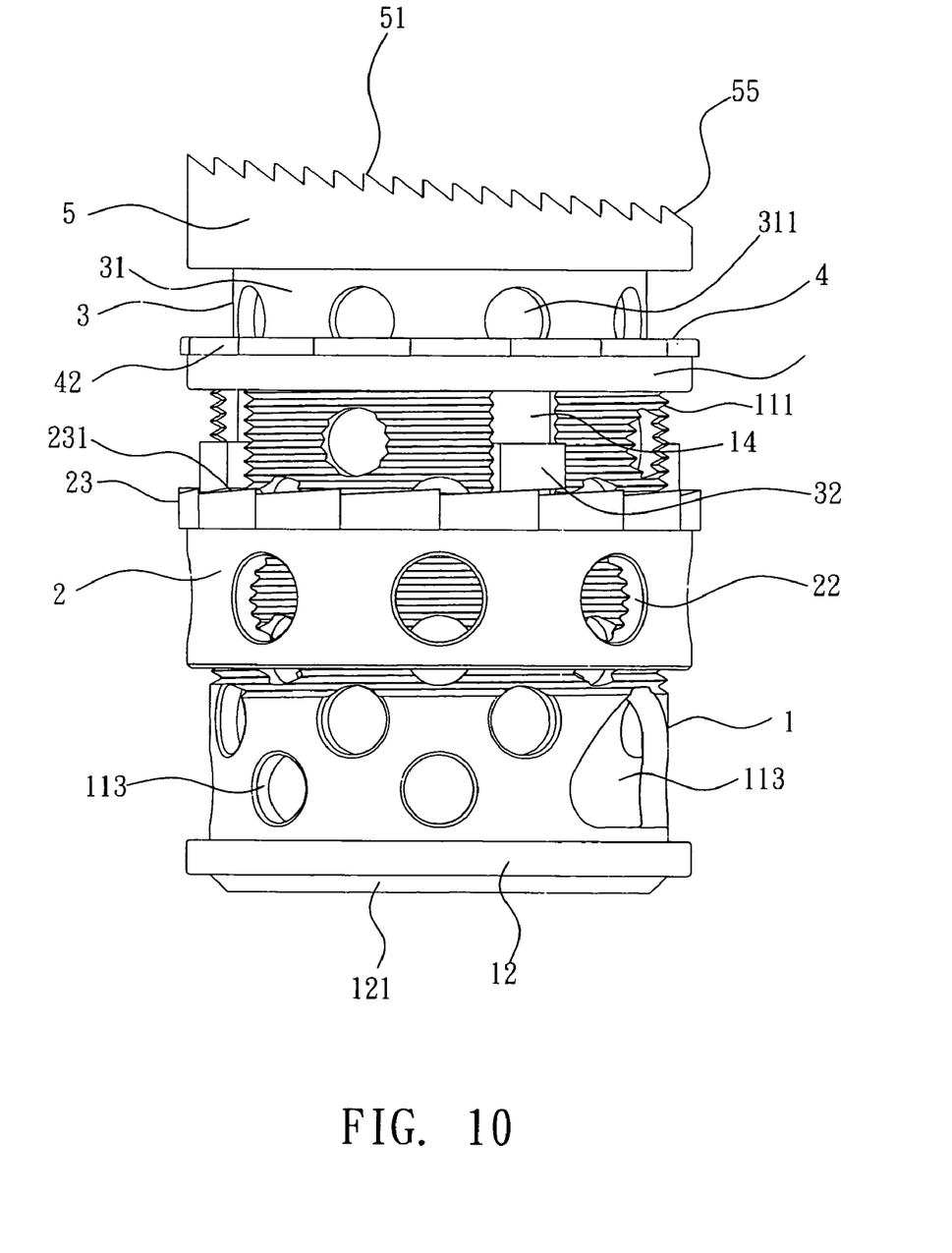
FIG. 10 is a side view of FIG. 9.

FIGS. 8~10 show an adjustable vertebral spacer in accordance with a second embodiment of the present invention in which like reference numbers indicate like parts. According to this second embodiment, the spacer body 1, the adjustment ring 2, the movable member 3 and the lock ring 4 are same as that of the aforesaid first embodiment. Therefore, no further detailed description about the relationship among the aforesaid parts. The major difference between this second embodiment and the aforesaid first embodiment is that the top endplate 5 according to this second embodiment is fixedly provided at the top side of the movable member 3 and has a sloping top wall 55. According to this second embodiment, the top protrusions 51 are linear teeth protruded from the sloping top wall 55.

If the angle of the vertebrae, more particularly, the fifth lumbar vertebrae is excessively high, a conventional adjustable artificial vertebral spacer tends to slip from place after the displacement. The invention eliminates this problem. As shown in FIG. 10, the greater the sloping angle of the sloping top wall 55 of the top endplate 5 in forward-backward direction relative to the vertebral body is, the deeper the engagement of the top protrusions 51 into the respective vertebral body will be, i.e., the design of the sloping top wall 55 enhances the stability. According to tests, the sloping angle is preferably within 16-degrees to fit different angles of different vertebral columns of different patients.

The top bearing wall 23 of the adjustment ring 2 is a ratchet 231 for engagement with the guide rods 32 of the movable member 3 to prevent slipping of the adjusting ring 2 relative to the movable member 3. This ratchet 231 design can also be employed to the adjustment ring 2 of the aforesaid first embodiment. Because the top endplate 5 is fixedly provided at the top side of the movable member 3, this second embodiment does not providing a tilting angle adjustment function and can only allow the user to adjust the height.

As described above, the invention allows the user to adjust the height of the adjustable vertebral spacer by means of rotating the adjustment ring to move the movable member vertically relative to the spacer body, and to lock the adjustable vertebral spacer at the adjusted height by means of rotating the lock ring toward the adjustment ring to have the guide rods of the movable member be sandwiched between the adjustment ring and the lock ring. Therefore, the adjustable vertebral spacer of the present invention provides a height adjusting function and a locking function. Further, the top protrusions and the bottom protrusions facilitate positive positioning of the adjustable vertebral spacer in between the adjacent upper vertebrae and lower vertebrae during the surgery, preventing slipping, sagging or collapsing of the vertebral spacer. Further, the top end plate that is provided at the top side of the movable member can be adjusted to the desired tilting angle subject to the angle of the adjacent upper vertebrae of the patient for positive engagement. Further, the spacer body provides a spacer body for accommodating self or transplanted bone graft, or a biomedical material, and the design of the peripheral circular through holes facilitate bone fusion and bone growth. The aforesaid features are not seen in prior art designs.

Although particular embodiments of the invention have been described in detail for purposes of illustration, various modifications and enhancements may be made without departing from the spirit and scope of the invention.

What is claimed is:
1. An adjustable vertebral spacer comprising:
a spacer body, said spacer body comprising a tubular body wall, a plurality of outer threads extending around said tubular body wall, a tubular space defined within said tubular body wall, a plurality of longitudinal guide slots cut through and downwardly extending from the topmost edge of said tubular body wall, a bottom endplate transversely located at a bottom side of said tubular body wall, a plurality of bottom protrusions downwardly protruding from said bottom endplate, and at least one bone- fusion hole cut through said bottom endplate in communication with the tubular space of said spacer body;

an adjustment ring threaded onto said outer threads of said spacer body and rotatable to move vertically upwards and downwards along said spacer body;

a movable member vertically movably inserted into the tubular space of said spacer body, said movable member comprising a tubular socket wall, a tubular space defined within said tubular socket wall, and a plurality of guide rods perpendicularly extended from the periphery of said tubular socket wall and respectively inserted through the longitudinal guide slots of said spacer body and supported on said adjustment ring for allowing said movable member to be moved with said adjustment ring vertically along said spacer body to a selected elevation through a rotation motion of said adjustment ring relative to said spacer body;

a lock ring threaded onto said outer threads of said spacer body to lock said guide rods of said movable member to said adjustment ring; and a top endplate connected to said movable member above the tubular space of said movable member and tiltable relative to said movable member, said top endplate comprising a plurality of top protrusions upwardly protruding from said top endplate, and at least one bone-fusion hole cut through said top endplate in communication with the tubular space of said movable member.

2. The adjustable vertebral spacer as claimed in claim 1, wherein said spacer body comprises a plurality of through holes transversely cut through said tubular body wall in communication with the tubular space of said spacer body; said movable member comprises a plurality of through holes transversely cut through said tubular socket wall in communication with the tubular space of said movable member; said adjustment ring comprises a plurality of through holes transversely cut through the periphery thereof.

3. The adjustable vertebral spacer as claimed in claim 1, wherein the top protrusions of said top endplate and the bottom protrusions of said bottom endplate are pointed teeth.

4. The adjustable vertebral spacer as claimed in claim 3, wherein the shape of said pointed teeth is one of a pyramid and a cone.

5. The adjustable vertebral spacer as claimed in claim 1, wherein the tubular space of said spacer body and the tubular space of said movable member are adapted for accommodating the bone graft of the patient, a transplanted bone graft, or a biomedical material.

6. The adjustable vertebral spacer as claimed in claim 1, wherein said adjustment ring has a top bearing wall at a top side thereof for supporting the guide rods of said movable member.

7. The adjustable vertebral spacer as claimed in claim 6, wherein said top bearing wall is a ratchet.

8. The adjustable vertebral spacer as claimed in claim 1, wherein said movable member comprises two mounting through holes aligned at two opposite sides and disposed near the topmost edge of said movable member; said top endplate comprises two pivot holes aligned at two opposite sides respectively pivotally connected to said mounting through holes of said movable member with a respective pivot member.

9. The adjustable vertebral spacer as claimed in claim 1, wherein said spacer body comprises at least one filling hole cut through said tubular body wall for the filling of at least one of a bone graft or biomedical material into the tubular space of said spacer body.

* * * * *